United States Patent [19]

Dimeff

[11] 4,303,919
[45] Dec. 1, 1981

[54] NON-CONTACTING DEVICE FOR SENSING MULTI-COMPONENT MOTION

[76] Inventor: John Dimeff, 5346 Greenside Dr., San Jose, Calif. 95127

[21] Appl. No.: 966,017

[22] Filed: Dec. 4, 1978

[51] Int. Cl.³ .................. G08C 19/10; A61C 19/04
[52] U.S. Cl. ........................ 340/870.37; 324/60 C; 324/61 R; 433/68
[58] Field of Search ............ 33/174 D, 174 L, 181 R, 33/363 R, 363 Q; 340/200, 189 M, 177 R, 870.37, 870.01; 324/61 R, 60 C, 60 R; 323/93; 433/24, 68; 318/662; 74/471 XY

[56] References Cited

U.S. PATENT DOCUMENTS

| | | | |
|---|---|---|---|
| 2,892,152 | 6/1959 | Buisson | 340/200 |
| 3,151,239 | 9/1964 | Lecroart et al. | 340/200 |
| 3,296,522 | 1/1967 | Wolfendale | 340/200 |
| 3,729,728 | 4/1973 | Hardway | 340/200 |
| 3,843,924 | 10/1974 | Wahlgren | 340/200 |
| 3,845,377 | 10/1974 | Shimotori | 324/61 R |

*Primary Examiner*—James J. Groody

*Attorney, Agent, or Firm*—Limbach, Limbach & Sutton

[57] ABSTRACT

Multi-component motions between two parts are sensed by this apparatus which comprises a first conductive element and a plurality of second conductive elements with a frame connected to the first and second elements to hold them closely spaced from each other but not in electrical contact. An electric oscillator is connected between the first element and the second elements to apply an oscillating signal between the first element and each of the second elements. A sensing circuit is connected to each of the second elements to separately detect changes in the protential between the first element and each of the second elements as the two parts are moved relative to each other and to produce a first set of separate electrical signals representative of such changes in the potential. These signals are then algebraicly combined in a plurality of predetermined combinations to thereby generate a second set of electrical signals which are each representative of the separate linear and rotative orthogonal components of the relative motion between the two parts.

11 Claims, 12 Drawing Figures

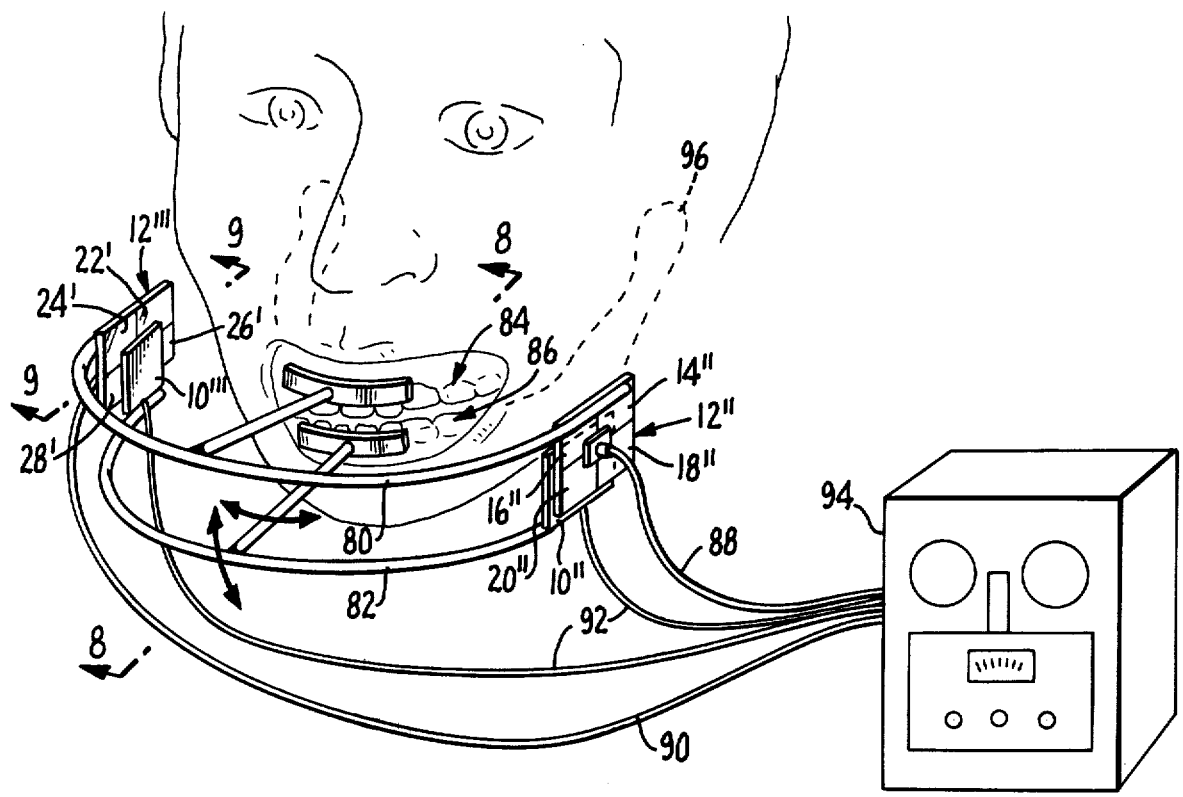
FIG. 7.
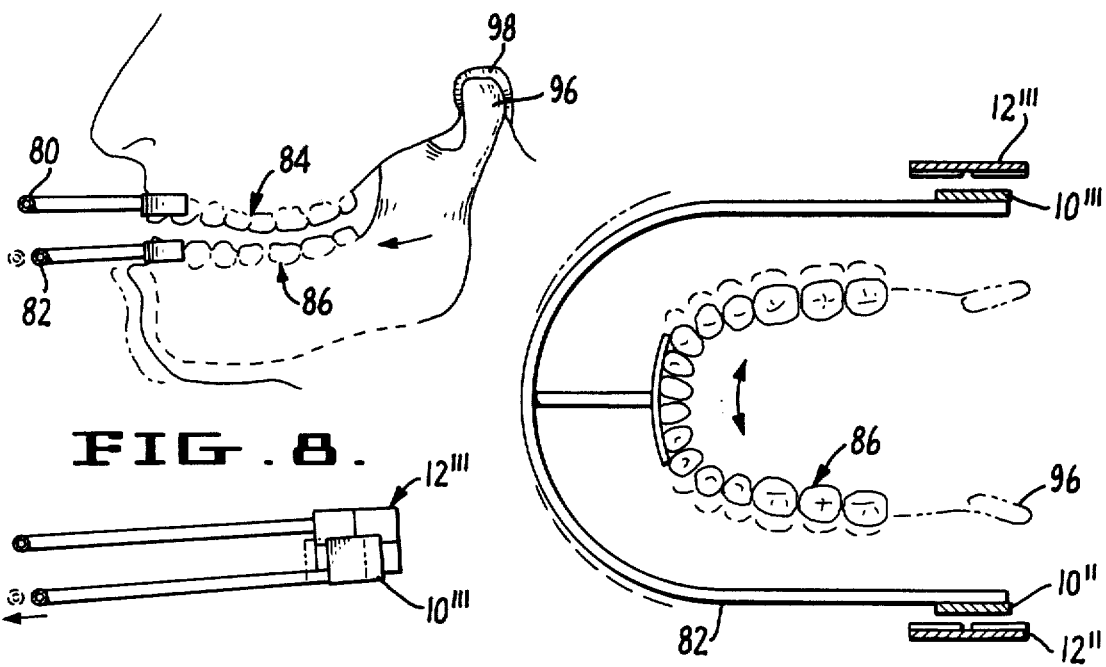
FIG. 8.
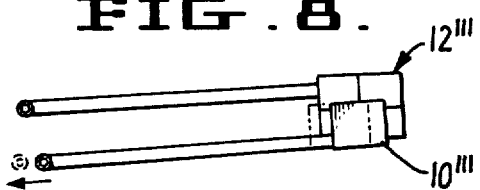
FIG. 9.
FIG. 10.

NON-CONTACTING DEVICE FOR SENSING MULTI-COMPONENT MOTION

BACKGROUND OF THE INVENTION

This invention relates to transducers for measuring lineal and rotative motions, and more particularly to a set of transducers for measuring relative motion between two parts.

Transducers for measuring deflections, proximities, forces, moments or other physical quantities of interest by attaching the transducers to the members specifically designed to respond to the physical quality of concern are well known. It is also known to arrange a multiplicity of such transducers into a composite transducer which is designed to measure several quantities simultaneously such as aerodynamic lift, drag, side force, pitching moment, yawing moment, and rolling moment. One drawback of prior art systems of this type, however, is that they are mechanically quite complex, suffer from easy misalignment, are effected by thermal expansion of the members to which they are attached and various other factors which limit accurate separation and measurement of the forces and moments of concern.

SUMMARY OF THE INVENTION

The above and other disadvantages of prior multi-component motion transducer systems are overcome by the present invention of an apparatus for sensing multi-component motions between two or more parts which comprises a first conductive element, a plurality of second conductive elements, and means for independently connecting the first element to one of the two parts and the second elements to the other of the two parts, with the first element being closely spaced from, but not in electrical contact with, each of the second elements and further being initially aligned with them. An electric oscillator is connected between the first element and the second elements to apply an oscillating voltage between them. Sensing means are connected to each of the second elements for separately detecting changes in the current between the first element and each of the second elements as the two parts move relative to each other. The sensing means produce a first set of separate electrical signals which are each representative of such changes and which are then algebraically combined in a plurality of predetermined combinations to generate thereby a second set of electrical signals which are each representative of the separate linear and rotative orthogonal components of relative motion between the two parts.

In the preferred embodiment of the invention, the first and second elements are rectangular in shape. The second elements in one embodiment each have equal corresponding dimensions, while in other embodiments, they have differing corresponding dimensions. The first and second elements can be planar, with the second elements being co-planar with each other or, in other embodiments, the first and second elements can be semi-cylindrical and coaxial.

While the applications of the present invention are numerous, in one preferred embodiment of the invention a double set of such transducers are supported at the opposite ends of two arc-shaped frames, one of which is attached to the maxillary teeth of a dental patient and the other of which is attached to the mandibulary set of teeth of the same patient. The sets of transducers are supported by these arc-shaped frames on either side of the patient's face and are aligned with the hinge axis of the patient's jaw. The patient is directed by the dentist to maneuver his or her jaw through a predetermined set of motions so that a set of relative motion signals are thereby generated by the transducers. These motion signals are recorded and are used to make a mechanical record of the patient's mandibular and occlusal pathway signatures. The complete apparatus for accomplishing this is described in the applicant's co-pending patent application entitled, Device for Recording and Reproducing Mandibular Motion, filed Dec. 4, 1978, now U.S. Pat. No. 4,204,326.

It is therefore an object of the present invention to provide a multi-component motion transducer having a minimal structural complexity.

It is another object of the invention to provide a multi-component motion transducer which is easily and simply manufactured.

It is still another object of the invention to provide a multi-component motion transducer having improved linearity and stability.

It is a still further object of the invention to provide a multi-component motion transducer which is environmentally insensitive.

The foregoing and other objectives, features and advantages of the invention will be more readily understood upon consideration of the following detailed description of certain preferred embodiments of the invention, taken in conjunction with the accompanying drawings.

BRIEF DESCRIPTION OF THE DRAWINGS

FIG. 7 is a perspective, diagrammatic view of an application of the multi-component transducer depicted in FIG. 1;

FIG. 8 is a side view, partly in section and taken generally along the lines 8—8 in FIG. 7;

FIG. 9 is a vertical, sectional view, taken generally along the lines 9—9 in FIG. 7;

FIG. 10 is a horizontal, sectional, diagrammatic view showing the alignment of the transducers depicted in FIG. 7 with the patient's mandibulary teeth;

DETAILED DESCRIPTION OF CERTAIN PREFERRED EMBODIMENTS

Figure 1:
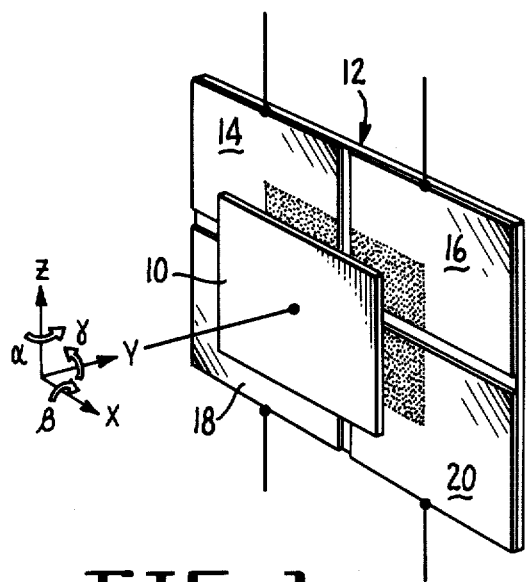
FIGS. 1 through 4 are perspective views of a multi-component transducer according to a first embodiment of the invention, with the FIGS. 2 through 4 illustrating the relative degrees of motion of the transducer.
Figure 2:
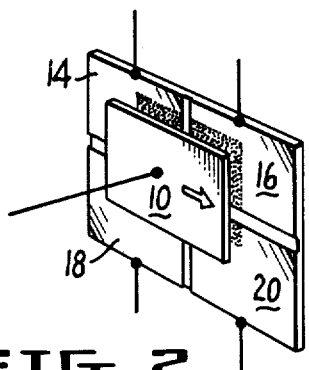
Figure 3:
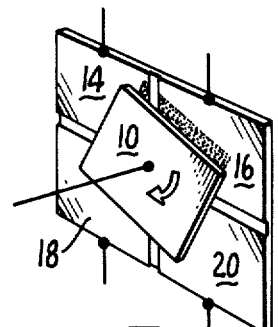

Referring now more particularly to FIG. 1, a first conductive, planar element 10 is placed in close proximity to a set 12 of co-planar, conductive, second elements 14, 16, 18, and 20. The element 10 and the set of elements 12 reside in parallel planes, at least initially. As will be described in greater detail with reference to FIG. 11, an oscillating voltage is applied between the element 10 and each element of the set of elements 12, to cause charges to be alternately attracted and repelled from the surfaces of the conductive elements 14 through 20. These charges are proportional to, among other factors, the mutual areas shared in the drawing by each segment with the overlapping element 10 and the spacing between the element 10 and the set of elements 12. From the figure, it can be seen that upward motion, as viewed in FIG. 1, of the element 10, that is, motion of the element 10 within its plane toward the top of FIG. 1, causes an increase in the area of overlap with respect to the elements 14 and 16, while causing a simultaneous decrease in the area of overlap of the elements 18 and 20. As illustrated in FIG. 2, motion of the element 10 within its plane, but toward the edges of the elements 16 and 20 that are rightwardly and downwardly disposed in FIG. 1 similarly, causes a simultaneous increase in the area of overlap of the elements 16 and 20, with a corresponding decrease in the overlap of the elements 14 and 18. With reference to FIG. 3, it can be seen that a clockwise rotation of the element 10 within its parallel plane, will cause an increase in the area of overlap of the elements 14 and 20, with a corresponding decrease in the area of overlap of the elements 16 and 18.

The differences in the alternating flow of charges to each of the elements 14 through 20 caused by the various motions of element 10 as described above, can be used as a measure of that motion.

Since the changes in charges detected by the elements 14 through 20 are also dependent on the proximal distance of the element 10 from the elements 14 through 20, it should be apparent that proximal motion of the element 10 in the direction Y shown in FIG. 1 will cause an increase in the current flowing to the elements 14, 16, 18 and 20 on the right side of the patient as shown in FIG. 7, while simultaneously causing a decrease in the current on his left side.

Figure 4:
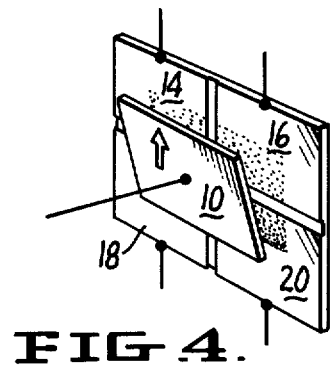

While such changes in proximal distance can occur by non-parallel rotation of the element 10 with respect to the set of elements 12 those rotations are limited in the application depicted in FIG. 7. Thus in reference to FIG. 4, it can be seen that rotation of the element 10 about a hypothetical axis which is parallel to the adjacent edges of the elements 14 and 18, causes a change in the charges which would be similar to that caused by downward lateral motion of the element 10 as viewed in FIG. 4 while simultaneously causing a change in the charges which would be similar to that caused by the upward lateral motion of the element 10 on the opposing side of the patient, relative to separate elements 22, 24, 26 and 28 on that opposing side. The second set of coplanar, conductive elements 22 through 28, essentially identical to the plate of elements 14 through 20, placed in proximal opposition to the element 10 on its opposite side from the elements 14 through 20 are also used to remove any ambiguity as to the actual motion of the element 10 relative to the set of elements 12, that is, whether the movement is translational or proximal.

Also shown in FIG. 1, is an orthogonal coordinate system containing three lineal coordinates X, Y, and Z, and three angular coordinates α, β and γ. With this arrangement, the interacting effects of unwanted rotation and proximal motion will be cancelled or greatly reduced and furthermore, some of these rotations can be separately measured. To accomplish this, charges referenced $Q_{14}$ through $Q_{28}$, which are the charges flowing periodically to the corresponding elements 14 through 28, are added or subtracted in predetermined combinations, according to the Table I below. A "plus" means the charges are added to the combination and a "minus" means the polarity of the charge is reversed before it is added, that is, it is subtracted from the combination:

TABLE I

|   | $Q_{14}$ | $Q_{16}$ | $Q_{18}$ | $Q_{20}$ | $Q_{22}$ | $Q_{24}$ | $Q_{26}$ | $Q_{28}$ |
|---|---|---|---|---|---|---|---|---|
| X | − | + | − | + | − | + | − | + |
| Y | + | + | + | + | − | − | − | − |
| Z | + | + | − | − | + | + | − | − |
| α | + | − | + | − | − | + | − | + |
| β | − | − | + | + | + | + | − | − |
| γ | − | + | + | − | − | + | + | − |

Figure 5:
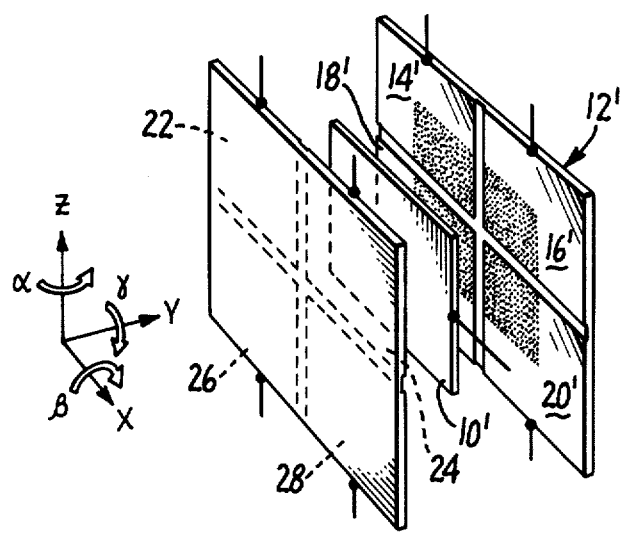
FIG. 5 is a perspective view of a multi-component transducer according to a second embodiment of the invention.

It is to be noted that the embodiment of FIG. 5 would give similar results by reversing the polarity of charges in the rows opposite γ and β, this reversal being caused by the relative values of the spacings of the active surfaces of 10 to the spacings of the plates 12 on the two cases. In either embodiment, to obtain the component of translational motion along the Y axis, all of the charges $Q_{14}$ through $Q_{20}$ are added together and all of the charges $Q_{22}$ through $Q_{28}$ are subtracted from the sum. Those skilled in the art will recognize that this table represents a method of obtaining approximations for the geometric quantities listed; that, for example, the signal derived as a measure of γ will more nearly be a measure of the trigonometric quantity sin γ; that the signal derived as a measure of Z will be more nearly a measure of the trigonometric product Z cos γ; and that the signal derived as a measure of X will be more nearly a measure of the product $X(\cos \gamma)^{-1}$.

Over the range of variation normally measured with such transducers, however, the range of γ is limited, and the value of sin γ closely approximates the value of γ, and the value of cos γ closely approximates 1, so that the tabular summations provide, in effect, a closely approximate measure of the quantities listed. Where a greater range of variability is encountered, the trigonometric functions and the multiplications or divisions required to correct the deviations related to large angular excursions can be accomplished by state of the art electronic integrated circuit devices such as are used in pocket calculators. Such devices incorporate a memory function in which the trigonometric functions are stored and which provide for electronic calculation based on those memory values.

From the above discussion it can be seen that several advantages directly result from the invention. One such advantage is that the structural complexity of the multi-component transducers are minimized because of the fact that the separate transducers are supported by a simple, integral structure, and are separated only by small insulating spaces. The construction of the transducers is also simplified because the transducer elements can be photo-etched, vapor deposited, sprayed, or painted on a common substrate during a single process.

The transducers can be made over a considerable range of sizes by the use of suitable photo techniques which allow a significant reduction in dimensions or, on the other hand, elements of large size can also be formed by spray painting. The improved linearity of the design of the invention has been demonstrated by the discussion above. The transducer system of the invention also has greater stability since arbitrary insulation substrates such as ceramic, glass or quartz or even conductive substrates which have first been overcoated with an insulating layer, can be used. Furthermore by mounting the plates on chemically and thermally resistant materials, or by overcoating them with such materials, the transducers can be made stable in normally threatening environments.

Figure 6:
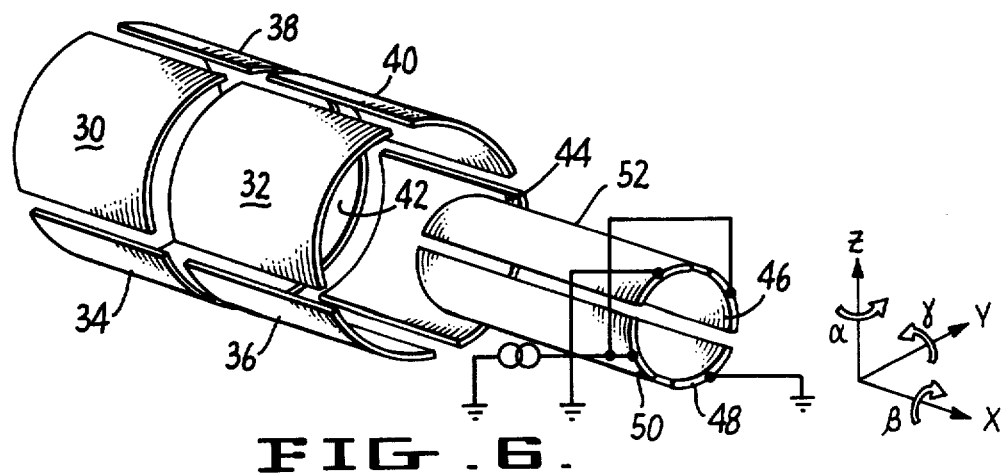
FIG. 6 is perspective view of a multi-component transducer according to a third embodiment of the invention.

While in the above discussion the transducer plates have been described as being planar, in other embodiments the plates may take different geometric forms. Referring now more particularly to FIG. 6 it can be seen that the rectangular embodiments depicted in FIGS. 1 through 5 and 7 can be altered to become a cylindrical embodiment. In the cylindrical embodiment individual semi-cylindrical sensing elements 30, 32, 34, 36, 38, 40, 42 and 44 together comprise a cylinder which is co-axial with an inner cylinder formed of oscillator driven semi-cylindrical elements 46, 48, 50 and 52. The elements 46 and 50 are connected directly to the oscillator whereas the elements 48 and 52 are grounded. The component charge flows from the individual sensing segments 30–44, inclusive, are summed in accordance with the following table where geometric corrections for large excursions are altered:

TABLE II

|   | $Q_{30}$ | $Q_{32}$ | $Q_{34}$ | $Q_{36}$ | $Q_{38}$ | $Q_{40}$ | $Q_{42}$ | $Q_{44}$ |
|---|---|---|---|---|---|---|---|---|
| X | − | + | − | + | − | + | − | + |
| Y | − | − | − | − | + | + | + | + |
| Z | + | + | − | − | + | + | − | − |
| α | + | − | + | − | − | + | − | + |
| β | − | − | + | + | + | + | − | − |
| γ | − | + | + | − | − | + | + | − |

Figure 12:
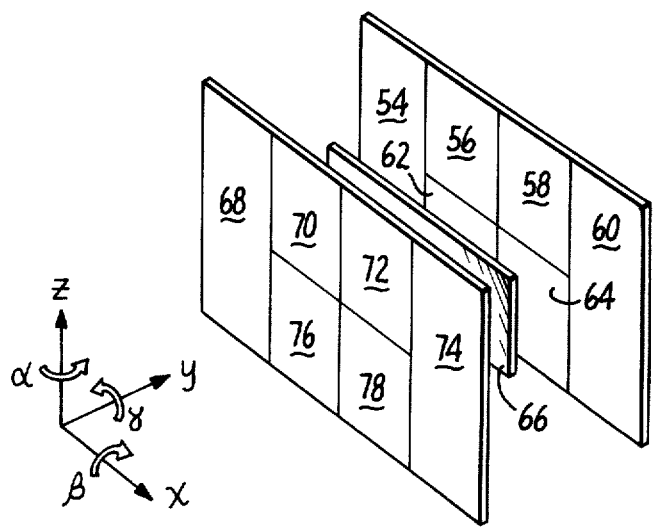
FIG. 12 is a perspective view of a multi-component transducer according to a fourth embodiment of the invention.

The distribution and shape of individual elements can be altered such as for example the modification of the planar rectangular format of FIG. 5 to that of FIG. 12 in which the end element pads 54, 60 and 68, 74 have dimensions which are generally twice as large as the corresponding dimensions of the inner element sensing pads 56, 58, 62, 64 and 70, 72, 76, 78 of the two opposed pad sets. As in the embodiment of FIG. 5, a single element 66 is interposed between these two element pad sets and is connected to an oscillator (not shown). The charge flows corresponding to the element pads 54 through 78 are summed according to the following table:

TABLE III

|   | $Q_{54}$ | $Q_{56}$ | $Q_{58}$ | $Q_{60}$ | $Q_{62}$ | $Q_{64}$ | $Q_{68}$ | $Q_{70}$ | $Q_{72}$ | $Q_{74}$ | $Q_{76}$ | $Q_{78}$ |
|---|---|---|---|---|---|---|---|---|---|---|---|---|
| X | − | − | + | + | − | + | − | − | + | + | − | + |
| Y | 0 | + | + | 0 | + | + | 0 | − | − | 0 | − | − |
| Z | 0 | + | + | 0 | − | − | 0 | + | + | 0 | − | − |
| α | 0 | − | − | 0 | − | + | 0 | + | −. | 0 | + | − |
| β | 0 | + | + | 0 | − | − | 0 | − | − | 0 | + | + |
| γ | 0 | − | + | 0 | + | − | 0 | − | + | 0 | + | − |

The relative locations of the parts comprising the multi-component transducer can be redistributed for reasons of convenience or for aesthetic reasons.

Referring now more particularly to FIGS. 7 through 10 an application of the transducer system according to the invention is illustrated in which two pairs of transducer sets are provided at the opposite ends of arc-shaped support frames 80 and 82 which are attached to a dental patient's maxilliary set of teeth and mandibular set of teeth 84 and 86, respectively. The arc-shaped frame 80 supports separate sets of conductive sensing pads 12″ and 12‴ at opposite sides the patient's jaw. The arc-shaped frame 82 supports separate single conducting elements 10″ and 10″ at opposite sides of the patient's jaw, each element being spaced apart from a separate one of the sensor pad sets 12″ and 12‴. The transducers 10″, 12″, 10‴ and 12‴ are connected by means of electrical cables 88, 90, and 92 to an electronic signal processing circuit 94. The manner in which the circuit 94 processes the signals received from the transducers will be described in greater detail hereinafter in reference to FIG. 11.

The arc-shaped frames 80 and 82, as best viewed in FIG. 8, support the transducers so that they are aligned along a hypothetical line which passes through the patient's condyle 96 and condyler socket 98. As is described more fully in the applicant's co-pending patent application entitled DEVICE FOR RECORDING AND REPRODUCING MANDIBULAR MOTION filed Dec. 4, 1978, and assigned Ser. No. 965,749 now U.S. Pat. No. 4,204,326, the signals derived from the circuit 94 are used to operate a servo-controlled milling machine which correspondingly grooves a plate to record the motions of the condyle 96 with respect to the socket 98 as the patient manipulates his or her jaw through a set of maneuvers as dictated by the dentist.

Figure 11:
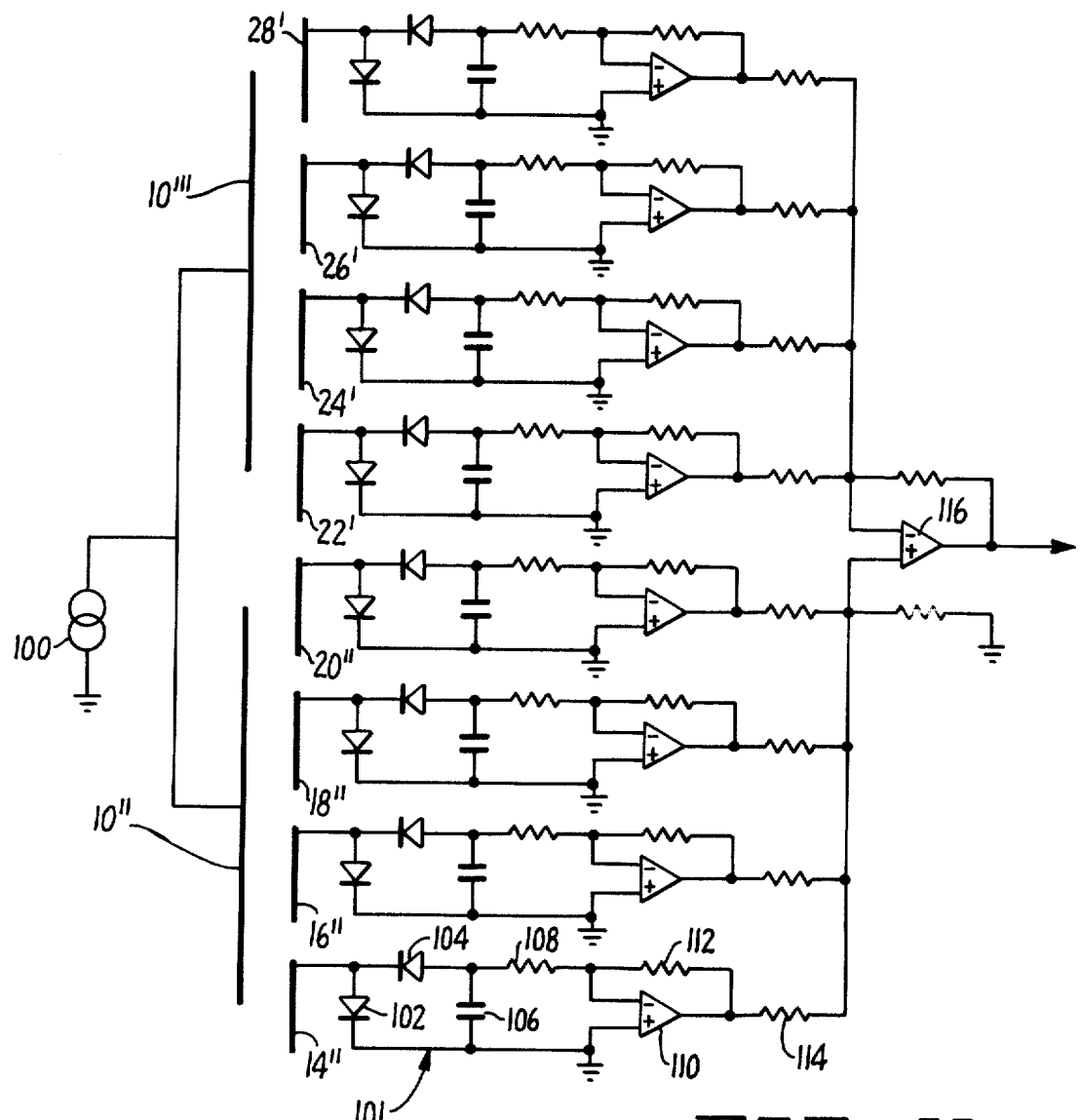
FIG. 11 is a schematic diagram of a portion of the electronic detection apparatus depicted in FIG. 7 for use with the embodiment depicted in FIG. 1.

Referring now more particularly to FIG. 11 a portion of the circuit 94 is illustrated by way of example. In the circuit depicted in FIG. 11 one output lead of an oscillator 100 is connected to the single element plates 10″ and 10‴. The other output lead of the oscillator 100 is connected to the circuit ground. Each of the opposed sensing elements 14″, 16″, 18″, 20″, 22′, 24′, 26′ and 28′ is provided with an independent signal processing circuit 101. Since all the circuits are substantially identical only one of the circuits will be described by way of example, it being understood that the description applies equally to the other circuits.

The sensing element 14″ is connected to the anode of a diode 102 whose cathode is connected to the circuit ground. The sensing element 14″ is also connected to the cathode of a diode 104 whose anode is connected to one lead of a capacitor 106 whose other lead is connected to the circuit ground. The anode of the diode 104 is also connected through a resistor 108 to the negative input of a differential amplifier 110. The positive input of the amplifier 110 is connected to the circuit ground. A feedback resistance 112 connects the output of the amplifier to the negative input. The output of the amplifier 110 is also connected through a resistance 114 to the positive input of a differential amplifier 116. It will be appreciated that the circuit 101, comprised of the elements 102 through 114, is repeated for each of the sensing elements 16″, 18″, 20″, 22′, 24′, 26′ and 28′.

In operation, the high frequency oscillator 110 produces a signal which is capacitively coupled to the sensing element plates. The signal derived from the plates is connected through the rectifying diodes 102 and 104 to create a stored charge on the capacitor 106. The magnitude of this stored charge is proportional to the magnitude of the signal from the oscillator, the area of overlap of the single element 10″ or 10‴ with respect to the elements 14" through 28', and is inversely proportional to the spacing between the elements 10" or 10'" and the sensing elements 14" through 28'.

The voltage corresponding to the stored charge on the capacitor 106 is amplified by the amplifier 110 by an amount which is determined by the ratio of the resistor 112 to the resistor 108. The amplified voltage is applied through the resistor 114 to the additive input of the amplifier 116. Similarly the outputs from the signal detecting circuits 101 connected to the elements 16", 18" and 20" are also connected to the additive input of the amplifier 116. The outputs from the circuits 101 connected to the elements 22', 24', 26' and 28' are connected to the negative input of the amplifier 116 and thus are subtracted from the sum of the signals supplied from the elements 14" through 20".

Referring back to Table I it can be seen that the input signals to the amplifier 116 correspond to the combination of charges necessary to determine the orthogonal quantity Y. That is, the aggregate of the inputs to the amplifier 116 are combined by the circuit to be proportional to the quantity Y.

Signals proportional to the remaining values X, Z, α, β and γ can be derived by similar predetermined combining of the output signals of the sensor detecting circuits 101. Such circuits connect the outputs of the detecting circuits 101 to either the plus (+) or the minus (−) input of the amplifier 116 in accordance with the convention indicated in the Table for the particular component of motion to be monitored. In the usual embodiment of the invention, the sensing plate signal detection circuits (elements 102, 104 and 106) could be located at the sensors with amplifying elements 108, 110 and 112 remotely located. Suitable isolating amplifiers (not shown) can also be interposed between detecting and amplifying elements, if necessary, so that the same signal detecting circuits 101 can be used to feed a plurality of different predetermined combining circuits, with low electrical impedance.

While in the above described embodiments the transducers preferably take the form of capacitively coupled elements in other, possibly less advantageous embodiments, the transducers could take the form of inductive coils which sense the position of a magnetized paddle, or inductive coils which sense the mutual coupling of the magnetic field of an oscillator activated paddle, or various other roughly analogous devices which duplicate the transducers described above.

The terms and expressions which have been employed here are used as terms of description and not of limitation, and there is no intention, in the use of such terms and expressions of excluding equivalents of the features shown and described, or portions thereof, it being recognized that various modifications are possible within the scope of the invention as claimed.

What is claimed is:

1. Apparatus for sensing multicomponent motions between two parts comprising
   a least a first conductive element,
   a plurality of second conductive elements, means for independently connecting the first element to one of the two parts and the second elements to the other of the two parts and with the first element being closely spaced from, but not in electrical contact with each of the second elements and further being initially aligned with them,
   an electric oscillator for generating an oscillating voltage, means for applying the oscillating voltage between the first element on the one hand, and each of the second elements, on the other hand,
   and sensing means connected to each of the second elements and the oscillator and including detecting means for separately detecting changes in the potential between first element and each of the second elements as the two parts move relative to each other and thereby change the spacing and alignment between the first element and the second elements and for producing a first set of separate electrical signals representative of such changes, and means for algebraically combining the electrical signals in a plurality of predetermined combinations to generate a second set of electrical signals which are each representative of the separate linear and rotative orthogonal components of the relative motion between the two parts.

2. Multi-component motion sensing apparatus as recited in claim 1 wherein the first and second elements are rectangular in shape.

3. Multi-component motion sensing apparatus as recited in claim 2 wherein the second elements have equal corresponding dimensions.

4. Multi-component motion sensing apparatus as recited in claim 1 wherein the first and second elements are planar and the second elements are co-planar.

5. Multi-component motion sensing apparatus as recited in claim 4 wherein the second elements are rectangular and co-planar, four of the second elements have the same corresponding dimensions and are contiguous, and two of the second elements are on opposite sides of the four, contiguous, second elements and have corresponding dimensions which are twice as large as the four, contiguous, second elements.

6. Multi-component motion sensing apparatus as recited in claim 1 wherein the second elements are divided into two sets and wherein the connecting means supports the first element inbetween the two sets of second elements.

7. Multi-component motion sensing apparatus as recited in claim 1 wherein the first and second elements are semicylindrical and share the same geometric axis of rotation.

8. Multi-component motion sensing apparatus as recited in claim 7 wherein the means for connecting the elements supports the first element in a co-axial relationship with the second elements.

9. Multi-component motion sensing apparatus as recited in claim 1 wherein the two parts whose relative motion is to be sensed are dental patient's mandible and maxilla and the connecting means comprise a first frame rigidly connected to the patient's mandibulary teeth and supporting one of either the first or the second set elements and a second frame rigidly connected to the patient's maxillary teeth and supporting the other of the first element or the second set of elements.

10. Multi-component motion sensing apparatus as recited in claim 9 further comprising a pair of first elements and a pair of sets of second elements and wherein the first and second frames are arc shaped and in registration with the arches of the patient's mandibulary and maxillary teeth, respectively, the first frame supporting one of the first elements on opposite sides of the patient's face and the second frame supporting one of the sets of second elements on opposite sides of the patient's face.

11. Multi-component motion sensing apparatus as recited in claim 1 further including a circuit ground and wherein the sensing means comprise a plurality of separate detecting circuits each connected to a separate one of the second elements and wherein each detecting circuit includes a capacitor and diode means connected in series with the circuit ground and the oscillator between the first element and one of the second elements and further including a plurality of separate resistors and separate amplifiers, each amplifier having an input connected to a separate one of the capacitors through a separate one of the resistors, and wherein the algebraic combining means are supplied with the outputs of the separate amplifiers.

* * * * *